(12) United States Patent
Smidt

(10) Patent No.: US 7,476,406 B1
(45) Date of Patent: Jan. 13, 2009

(54) MULTIFACETED WEIGHT CONTROL SYSTEM

(75) Inventor: Carsten Smidt, Provo, UT (US)

(73) Assignee: NSE Products, Inc., Provo, UT (US)

(*) Notice: Subject to any disclaimer, the term of this patent is extended or adjusted under 35 U.S.C. 154(b) by 325 days.

(21) Appl. No.: 11/131,909

(22) Filed: May 17, 2005

Related U.S. Application Data

(60) Provisional application No. 60/572,184, filed on May 17, 2004.

(51) Int. Cl.
*A61K 36/82* (2006.01)
*A61K 36/296* (2006.01)
*A61K 36/73* (2006.01)

(52) U.S. Cl. ............ 424/729; 424/765; 424/777; 514/909

(58) Field of Classification Search .......... None
See application file for complete search history.

(56) References Cited

U.S. PATENT DOCUMENTS

| | | | |
|---|---|---|---|
| 6,224,873 B1 * | 5/2001 | Jones | |
| 2001/0001307 A1 * | 5/2001 | Ueda et al. | 514/563 |
| 2002/0076456 A1 * | 6/2002 | Stogniew et al. | 424/769 |
| 2002/0192308 A1 * | 12/2002 | Mamana | 424/729 |
| 2004/0171694 A1 * | 9/2004 | Van Laere et al. | 514/574 |

FOREIGN PATENT DOCUMENTS

| | | | |
|---|---|---|---|
| EP | 001295535 A2 * | 9/2002 | |
| EP | 1295535 A2 * | 3/2003 | |
| JP | 03027264 A * | 2/1991 | |
| JP | 09227398 A * | 9/1997 | |
| JP | 2002173437 A * | 6/2002 | |
| WO | WO 9623811 A1 * | 8/1996 | |

OTHER PUBLICATIONS

Vaskonen, T et al. British Journal of Nutrition (Feb. 2002); 87(3): 239-245. Effects of calcium and plant sterols on serum lipids in obese Zucker rats on low-fat diet.*
Chantre, P et al. Phytomedicine (Jan. 2002); 9(1): 3-8. Recent findings of green tea extract AR25 (Exolise) and its activity for the treatment of obesity.*
Homma et al. Journal of Pharmacy and Pharmacology (1994); 46(4): 305-309. A novel 11-beta-hydroxysteroid dehydrogenase inhibitor contained in Saiboku-T, a herbal remedy for steroid-dependent bronchial asthma.*
Horigome H et al. Planta Medica (Feb. 2001) ; 67(1) : 33-37. Magnolol from *Magnolia officinalis* inhibits 11 beta-hydroxysteroid dehydrogenase without increases of corticosterone and thymocyte apoptosis in mice.*
Yang J et al. Shenyang Yaoke Daxue Xuebao (1998) ;15(2): 94-97. Immunopotentiation of total flavones of Epimediumm (TFE) on immunodepressed mice.*
Liu F et al. Journal of Nutrition (Sep. 2001); 131(9): 2242-2247. An extract of *Lagerstomia speciosa* L. has insulin-glucose uptake stimulatory and adipocyte differentiation activities in 3T3-L1 cells.*
Ikegaya, K. Jarq (1990); 24(1): 49-53. Determination of chemical constituents in processed green tea by near infrared analysis.*
U1, Yang J et al. Shenyang Yaoke Daxue Xuebao (1998) :15(2): 94-97. Immunopotentiation of total flavones of Epimediumm (TFE) on immunodepressed mice.*
V1, Liu F et al. Journal of Nutrition (Sep. 2001); 131(9): 2242-2247. An extract of *Lagerstomia speciosa* L. has insulin-glucose uptake stimulatory and adipocyte differentiation activities in 3T3-L1 cells.*
Choo, JJ et al. Journal of Nutritional Biochemistry (Jan. 2003); 14(11): 671-676. Green tea reduces body fat accretion caused by high-fat diet in rats through β-adrenoceptor activation of thermogenesis in brown adipose tissue.*
De Tommasi, N et al. Planta Medica (1991); 57(5): 414-416. Hypoglycemic effects of sesquiterpene glycosides and polyhydroxylated triterpenoids of *Eriobotyra japonica*.*
Rhee, S-J et al. Han'guk Sikp'um Yongyang Kwahak Hoechi (1997), 26(6), 1187-1193. Effects of green tea catechins on liver 3-hydroxy-3-methylglutaryl coenzyme A reductase activity and serum lipid levels in streptozotocin-induced diabetic rats. Abstract.*
Björntorp, P et al. Nutrition (2000); 16(10): 924-936. Obesity and cortisol.*
Sun et al. Shenyang Yaoke Daxue Xuebao (1995), 12(4): 266-9: 306. A study on the active constituents of *Epimedium koreanum* Nakai. Abstract.*

* cited by examiner

*Primary Examiner*—Michele Flood
(74) *Attorney, Agent, or Firm*—Thorpe North & Western LLP

(57) ABSTRACT

Weight-controlling or modulating compositions, systems, and methods are disclosed and described. Such compositions may include a thermogenic ingredient, a cortisol modulating ingredient, and a carbohydrate craving controlling ingredient. Furthermore, such compositions may be used in connection with exercise and dietary modifications or restrictions.

20 Claims, No Drawings

MULTIFACETED WEIGHT CONTROL SYSTEM

PRIORITY DATA

This patent application claims priority to U.S. Provisional Patent Application Ser. No. 60/572,184 filed May 17, 2004, which is incorporated herein by reference in its entirety.

FIELD OF THE INVENTION

The present invention relates generally to weight control compositions systems, and methods. Accordingly, the present invention involves the areas of botany, nutritional and health sciences, chemistry and medicine.

BACKGROUND OF THE INVENTION

One of the major issues facing society today is the growing number of people who are overweight or obese. Unfortunately, weight gain is often a problem that cascades into obesity due to the physiological and behavioral issues associated with weight gain, such as reduced activity and accelerated fat storage. Therefore, once a person begins to gain weight it can be very difficult to reverse course and take control of their weight.

In response to the large number of individuals who experience severe weight control problems, many weight management programs have been designed and promoted by the health industry. Despite their apparent differences, most of such programs share a common single mechanism of action, namely, to increase the ratio of calories burned per day to the amount of calories consumed per day. Many programs attempt to accomplish this by increasing the basal metabolic rate (BMR) through exercise or ingesting dietary stimulants (i.e. thermogenic supplements), such as ephedra, caffeine, and citrus aurantum among others. Other programs attempt to reduce or limit the number of calories consumed, some by simply tracking and limiting the calories, and others by the use of appetite suppressants. In still other cases, supplements are provided which are supposed to reduce or block the body's absorption of food ingested, such as carbohydrate blockers, or fat trappers. While a number of these programs have resulted in short term weight loss, many have also proven to have certain adverse health consequences, and some even have been thought to induce physiological responses that actually cause weight gain in the long run.

Of the above-recited mechanisms, exercising in order to increase the number of calories burned per day is probably the mechanism which has been most widely advocated by the health care industry. The calories that are burned during exercise can come from food that has recently been consumed that has not yet been reconfigured as fat storage within the body, or it can come from the body's stored energy, such as fat deposits, depending on the type of exercise employed. Accordingly, the amount of food, as well as the type and frequency of exercise, can impact the success of any exercise regimen. Improper nutrition intake coupled with exercise can actually cause the body to begin a vicious cycle of building fat after meals, and then not using all of the recently stored fat during the next exercise phase. The unfortunate result is an overall increase in stress and weight over time.

Some recent fad diets have focused on what people eat rather then when or how much they eat. While these diets can often result in dramatic short-term weight loss, restricting the type of food can also limit the opportunity to take in proper nutrients. For example, low-fat diets are typically higher in fiber and carbohydrates due to an increase in the volume of fruits and vegetables that are consumed, but may not provide enough fat and/or protein. On the other hand, low-carbohydrate diets, such as the Atkins diet, can result in weight loss because the intake of fat and protein can be self-limiting. However, the low-carbohydrate diet can fail with respect to nutritional value because of the elimination of many sources of Vitamin E, Vitamin A, Vitamin B6, thiamin, folate, calcium, magnesium, zinc, potassium and/or dietary fiber. Accordingly, these fad diets can result in an improper nutritional balance, and can require supplementation in order for the dieter to stay healthy. Additionally, any time the sources of nutrients or the types of nutrients are limited, the body can become stressed in attempting to function properly without the proper fuel.

In summary, most current weight control programs employing a single modality, either deprive the body of required nutrients, or are likely to actually induce or contribute to weight gain over a long period of time. This is in part due to the cycle of unsustainable rapid weight loss, followed by failure to maintain the program efforts, followed by a weight gain to a level that is actually higher than previous. In many cases, the failure to maintain the program may be due to the loss of key nutrients and resultant deterioration of overall health. In other cases, the failure to maintain the program may be due to the physical discomfort or difficulty of staying on the program.

As a result, weight management and loss systems that safely and effectively, facilitate long term weight control without compromises in proper nutrition, or other adverse effects continue to be sought.

SUMMARY OF THE INVENTION

Accordingly, the present invention provides compositions, systems and methods that safely, and effectively, facilitate long term weight control by employing a multifaceted approach to address multiple weight loss factors simultaneously. Such compositions will generally include a combination of at least three components, namely, at least one thermogenic component, at least one cortisol modulating component, and at least one carbohydrate craving controlling component, each in a therapeutically effective amount. In one aspect, the thermogenic component may include calcium and a green tea extract containing at least one member selected from the group consisting of a green tea methylxanthane and a green tea polyphenol. In another aspect, the green tea polyphenol can be a catechin. In one aspect, the cortisol modulator component may include one or more of the following: a magnolia bark extract, an epimedium extract, L-theanine, and beta-sitosterol. In yet another aspect, carbohydrate craving controller component may include a banaba leaf extract, MuGua extract (*Fructus chaenomelis*), Pi pa ye extract (*Eriabotrya japonica*) vanadium and chromium. The above-recited general ingredients may further be combined with an effective amount of an inert carrier in order to form a composition of a specific dosage type. Examples of suitable carriers for the production of oral dosage forms, such as tablets or capsules may include without limitation, gelatin, microcrystalline cellulose, magnesium stearate, silicon dioxide, and combinations thereof.

In accordance with the present invention, the components of the weight controlling composition can be present in variable amounts as required to provide a composition having certain desired characteristics. However, in one aspect, the thermogenic component can have a daily dose range from about 500 mg to about 3,000 mg. In another aspect, the thermogenic component can have a daily dose of about 1,500 mg. When included as part of the thermogenic component, the green tea extract can have a daily dose range from about 350 mg about 2,000 mg. More particularly, the green tea extract can have a daily dose of about 1,000 mg. Also, the green tea polyphenol can be a catechin. Additionally, the calcium can have a daily dose range from about 150 mg to about 1,000 mg, which can be a daily dose of about 500 mg. A variety of forms of calcium may be used, such as calcium carbonate, calcium citrate, calcium propionate, etc. However, in one aspect, the calcium can be dicalcium malate.

The weight controlling composition can include the cortisol modulator component in a daily dose range from about 300 mg to about 2000 mg. In a more detailed aspect, the cortisol modulator component can have a daily dosage of about 870 mg. The magnolia extract can have a daily dosage range from about 100 mg to about 600 mg. In one aspect, the magnolia extract can have a daily dosage of about 300 mg. The epimedium extract can have a daily dosage range from about 100 mg to about 600 mg. More particularly, the epimedium extract can have a daily of about 300 mg. The L-theanine can have a daily dosage range from about 50 mg to about 300 mg. In a more detailed aspect, the L-theanine can have a daily dosage of about 150 mg. The beta-sitosterol can have a daily dosage range from about 40 mg to about 240 mg. In some aspects, the beta-sitosterol can have a daily dosage of about 120 mg.

In another aspect of the present invention, the carbohydrate craving controller component can have a daily dosage range from about 10 mg to about 65 mg. In some embodiments, the carbohydrate craving controller component can have a daily dosage range of about 32 mg. In one aspect, the banaba leaf extract can have a daily dosage range from about 10 mg to about 64 mg. In another aspect, the banaba leaf extract can have a daily dosage of about 32 mg. The chromium can have a daily dosage range from about 66.7 mcg to about 400 mcg. More particularly, the chromium can have a daily dosage of about 200 mcg. Additionally, the chromium can be a chromium chelate. In yet another aspect, the vanadium can have a daily dosage range from about 10 mcg to about 60 mcg. In a further aspect, the vanadium can have a daily dosage of about 30 mcg. Also, the vanadium can be vanadyl sulfate.

In yet another aspect of the present invention, the thermogenesis, or thermogenic component and the cortisol modulator component can be present in a weight ratio of from about 3:2 to about 5:3. Additionally, the thermogenic component and the carbohydrate craving controller can be present in a weight ratio of from about 50:1 to about 300:6.4. Furthermore, the cortisol modulator component and the carbohydrate craving controller can be present in a weight ratio of from about 30:1 to about 200:6.4.

While a variety of dosage forms may be employed by the present composition, in one aspect of the present invention, the weight controlling composition can be an oral dosage form. Examples of suitable oral forms include without limitation, granules or powders, tablets, capsules, gel capsules, liquids, syrups, elixirs, and suspensions. In one aspect, the oral composition can be a capsule.

An additional embodiment of the present invention provides methods for controlling the weight of a subject in need thereof. Such method can include the steps of: elevating thermogenic activity within the subject; controlling the subject's carbohydrate cravings; and controlling the subject's cortisol level. In one aspect, all of these steps can occur simultaneously. In another aspect, such steps can be induced by administering a weight controlling composition as recited herein. In yet another aspect, the method can further include the step of increasing the subject's level of exercise. In still another aspect, the method can further include the step of providing the subject with a healthy diet. In the methods described herein, controlling the weight can either be reducing the weight of the subject, or is preventing the weight of the subject from increasing. In a further aspect, controlling the subject's carbohydrate cravings can be reducing the subject's carbohydrate cravings. Furthermore, controlling the subject's cortisol level can be reducing the subject's cortisol level.

In accordance with the compositions and methods described herein, the weight controlling composition can be administered on a daily basis as needed or according to a specific and customized dosing regimen. In one aspect, the weight loss composition can be administered at least once a day. In another aspect, administration can occur multiple times in a single day. In yet another aspect, the weight loss composition can be administered at least 3 times a day. In an additional aspect, administration can occur a specified time prior to a meal. In a further aspect, the weight loss composition can be administered at about the same time as the subject consumes a meal.

Of course, the duration of administration may be dictated by the individual needs of the subject engaged in the weight control program or method. However, in one aspect, the weight loss composition can be administered in a regimen having a duration of at least one week. In still another aspect, the weight loss composition can be administered in a regimen having a duration of at least one month. Furthermore, the weight loss composition can be administered in a regimen having a duration of about 3 months to about 24 months.

There has thus been outlined, rather broadly, the more important features of the invention so that the detailed description thereof that follows may be better understood, and so that the present contribution to the art may be better appreciated. Other features of the present invention will become clearer from the following detailed description of the invention, or may be learned by the practice of the invention.

DETAILED DESCRIPTION

Reference will now be made to exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Further, it is to be noted, that the formulations of the present invention can include a number of ingredients that may be obtained from either natural or artificial sources (i.e. synthetically). In addition, many ingredients may be initially obtained from a natural source, and then processed or altered to obtain or refine specific products therefrom. As recited herein, many natural sources are referred to by either a commonly known or scientific name. It is to be understood that the recitation of such a name refers not only to the specific source, but also to various specific parts of such a source, including components that are separated or extracted therefrom. For example, the term "kava" refers not only to the plant having the Latin name piper methysticum, as well as other closely related species, but also includes specific parts thereof, such as branches, roots, fruit, etc., as well as extracts or other preparations obtained from such parts.

DEFINITIONS

In describing and claiming the present invention, the following terminology will be used in accordance with the definitions set forth below.

The singular forms "a," "an," and, "the" include plural referents unless the context clearly dictates otherwise. Thus, for example, reference to "a carrier" includes reference to one or more of such carriers, and reference to "an active agent" includes reference to one or more of such active agents.

As used herein, "cortisol" refers to an adrenal cortical steroid hormone. Cortisol has the chemical general structure of:

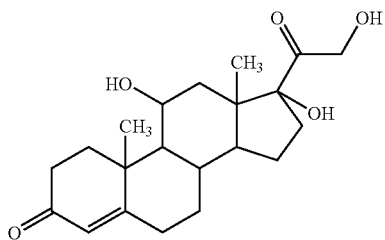

and is well known to those skilled in the art, by other names that may be used interchangeably therewith, such as hydrocortisone. As such, a "cortisol modulator" refers to a substance that controls, reduces, or otherwise ameliorates serum cortisol levels to a selected degree when administered in a therapeutically effective amount.

As used herein, "anti-stress ingredient" refers to a substance which moderates or reduces the physiological symptoms or indicators of stress, when administered to a subject in a therapeutically effective amount. As will be recognized by those of ordinary skill in the art, a reduction in stress may be measured by a variety of parameters, including certain physiological indicators, such as brain wave and other neurological activity, the presence and amount of certain substances in the blood, such as adrenaline, or by certain vitamin and mineral deficiencies, including chromium and pantothenic acid deficiencies. Further, stress reduction may in some aspects be measured by observance of a subject's mood, attitude, disposition, etc., as well as by questioning a subject as to their feelings or mental state.

As used herein, a "positive health benefit" imparting agent or substance refers to any substance either synthesized or extracted from a natural source, which is beneficial to the human body when consumed in an effective amount. Accordingly, weight control, thermogenesis, cortisol modulation, or a carbohydrate craving control may result upon the administration of a therapeutically effective amount of a positive health benefit imparting agent, or such an agent may provide a contributory effect. Examples of general positive health benefit imparting agents include, without limitation, vitamins, minerals, anti-oxidants, amino acids, and various botanical and herbal extracts.

As used herein, "thermogenic agent," thermogenic component," or other derivative thereof refers to a bioactive agent that effectively raises or elevates the basal metabolic rate (BMR) in a subject to which the agent is administered. A number of such agents are known in the art, including without limitation, green tea extracts, green tea polyphenols, green tea flavanols, green tea catachins, and calcium. Such thermogenic components can be combined with other basal metabolic rate enhancing agents to provide an optimal thermogenic effect, as is known in the art.

As used herein, a "metabolic stimulant" or other derivative refers to a bioactive agent that can stimulate an increase in the metabolic process. Such metabolic stimulants are well known in the art and can include ephedra, citrus aurantium, yohimbe, and coleus forskohli. Such agents may be combined with other stimulants, such as caffeine in order to provide an optimal thermogenic effect, as is known in the art.

As used herein, the terms "formulation" and "composition" may be used interchangeably. The terms "drug," "active agent," "bioactive agent," "pharmaceutically active agent," "nutraceutical active agent," "pharmaceutical," and "nutraceutical," are also used interchangeably to refer to an agent or substance that has measurable specified or selected physiologic activity when administered to a subject in an effective amount. These terms of art are well-known in the pharmaceutical, nutraceutical, and medicinal arts.

As used herein, the terms "administration," and "administering" refer to the manner in which a formulation or composition is introduced into the body of a subject. Administration can be accomplished by various art-known routes such as oral, parenteral, transdermal, inhalation, implantation, etc. Thus, oral administration can be achieved by swallowing, chewing, and/or sucking of an oral dosage form comprising an active agent. Parenteral administration can be achieved by injecting a drug composition intravenously, intra-arterially, intramuscularly, intrathecally, or subcutaneously, etc. Transdermal administration can be accomplished by applying, affixing, pasting, rolling, attaching, pouring, pressing, rubbing, etc., of a transdermal preparation onto a skin surface. These and additional methods of administration are well-known in the art.

The terms "effective amount" and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating a condition for which the active agent is known to be effective. Various biological factors may affect the ability of a substance to perform its intended task. Therefore, an "effective amount" or a "therapeutically effective amount" may be dependent on such biological factors. Further, while the achievement of therapeutic effects may be measured by a physician or other qualified medical personnel using evaluations known in the art, it is recognized that individual variations and responses to treatments may make the achievement of therapeutic effects a subjective decision. Accordingly, the determination of an effective amount is well within the ordinary skill in the art of pharmaceutical, nutraceutical, herbaceutical, and health sciences. See, Meiner and Tonascia, "Clinical Trials: Design, Conduct, and Analysis," *Monographs in Epidemiology and Biostatistics*, Vol. 8 (1986), incorporated herein by reference.

Accordingly, when discussed herein, the thermogenic component can be present in a therapeutically effective amount, which is an amount that is sufficient to support thermogenesis within the subject. Such support of thermogenesis can include an increase in the thermogenesis within the subject, or any increase in the metabolic process, which can be an increase in the basal metabolic rate. Additionally, when discussed herein, the cortisol modulator component can be present in a therapeutically effective amount that is sufficient to modulate the cortisol in the serum of the subject, or to lower the cortisol level within the subject. Further, when discussed herein, the carbohydrate craving controller component can be present in a therapeutically effective amount that is sufficient to control the carbohydrate craving within the subject by either reducing the carbohydrate craving, or preventing the carbohydrate craving from increasing.

As used herein, the terms "carrier" "pharmaceutically acceptable carrier" or "inert carrier" refer to a carrier vehicle with that can be combined with a bioactive agent, such as any of the components in the weight controlling composition, to achieve a specific dosage form. As a generally principle, carriers must not react with the bioactive agent in a manner which substantially degrades or otherwise adversely affects the bioactive agent. Other "inactive" ingredients may also be used in creating the weight controlling compositions described herein, and having specifically desired properties or dosage forms, and will be readily recognized by those of ordinary skill in the art.

As used herein, the term "subject" refers to a mammal that may benefit from the administration of a weight controlling composition or method as recited herein. Most often, the subject will be a human, and may need to lose weight or to prevent their weight from increasing.

The term "extract," when used in connection with any of the components or ingredients within the weight controlling compositions described herein, refers to one or more active agents, or a composition containing such, that is obtained from the source plant of such ingredient, or a portion of the source plant. The extract may be derived from any aspect of the source plant as long as the extract contains the proper substances to elicit the desired result when combined with the other ingredients of the weight controlling composition. As will be recognized by those of ordinary skill in the art, extracts may be either crude or refined to a selected degree in order to isolate certain active agents. A number of extraction processes can be employed to produce compositions of various types, and will be recognized by those of ordinary skill in the art. Also, an extract can be in any physical phase, consistency, and/or form, and is not limited to being a solid, a dry powder, a liquid, a paste, or other physical characteristic designation.

As used herein, the terms "inhibit," "inhibiting," or any other derivative thereof refers to the process of holding back, suppressing or restraining so as to block, prevent, limit, or decrease a rate of action or function. The use of the term is not to be misconstrued to be only of absolute prevention, but can be a referent to any minute incremental step of limiting or reducing a function through the full and absolute prevention of the function.

As used herein, "reduce" or "reducing" refers to the process of decreasing, diminishing, or lessening, as in extent, amount, or degree of that which is reduced. The use of the term with respect to a subject's weight, cortisol levels, or carbohydrate cravings can include any incremental step that results in less weight, lower cortisol levels, and/or a diminished desire to each carbohydrates in comparison to the state prior to being "reduced." Additionally, the use of the term can include from any minimal decrease to absolute abolishment of any of these physiological processes or effects.

As used herein, "mc" or "micro" when used in combination with a unit of measurement denotes the standard unit to be divided by one million, or multiplied by $1 \times 10^{-6}$. For example, "mcg" refers to a microgram, and "100 mcg" refers to a 100 microgram amount of a substance. Accordingly, the prefix "micro," which is well known by one or ordinary skill in the art can be referred herein by the abbreviation "mc."

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a concentration range of 0.01 to 6 wt % should be interpreted to include not only the explicitly recited concentration limits of 0.01 wt % and 6 wt %, but also to include individual concentrations such as 0.3 wt %, 0.6 wt %, 2.0 wt %, 2.3 wt %, 3.7 wt %, 5.4 wt %, and sub-ranges such as 0.2-2.3 wt %, 1.3-3.9 wt %, 2.9-5.1 wt %, etc. This interpretation should apply regardless of the breadth of the range or the characteristic being described, and should apply to ranges having both upper and lower numerical values, as well as open-ended ranges reciting only one numerical value.

THE INVENTION

The applicants have discovered that a formulation containing a thermogenic component, a cortisol modulator component, and a carbohydrate craving controller component can be used in controlling the weight of a subject when administered thereto. Also, the Applicants have discovered methods of controlling the weight of a subject by utilizing a multifaceted approach that includes elevating thermogenic activity within the subject, controlling the subject's carbohydrate cravings, and controlling the subject's cortisol level. As such, the present invention extends not only to the composition of the formulation, but also to the methods of using the formulation as indicated.

In accordance with the present invention, one embodiment can provide a weight controlling composition for administration to a subject that may be in need of losing weight or in need of preventing weight gain. Accordingly, the weight controlling composition can contain a therapeutically effective amount of a thermogenic component which includes calcium and a green tea extract. In accordance therewith, the calcium can be any calcium compound that can be used in a supplement, including calcium carbonate, calcium phosphate, dicalcium malate, calcium lactate, calcium gluconate, calcium citrate, and calcium chelates. In accordance therewith, the green tea extract can include a green tea methylxanthane, such as caffeine, a theobromine and/or a theophylline. Additionally, the green tea extract can include a green tea polyphenol, such as a favanol, which can include green tea catechins. Such green tea catechins can include epigallocatechin-3-gallate, epigallocatechin, epicatechin-3-gallate, epicatechin, gallocatechin, and/or catechin. The green tea extract can also include a lignin, an organic acid, and other phenolic compounds, such as flavanol glycosides, flavanol depsides, chlorogenic acid, coumarylquinic acid, and 3-galloylquinic acid (theogallin). In one aspect of the invention, the green tea can be from *Camellia senesis*, and can be from about a 20:1 to about a 70:1 extract. Additionally, the green tea extract can contain up to about 97 wt % polyphenols. Alternately, the green tea extract can have a minimum of about 97 wt % polyphenols. In still another aspect, the green tea extract can include green tea saponins.

These thermogenic ingredients can be individually included, or may be selectively combined in the formulation of the present invention in order to achieve a specific result. Moreover, the source and amount of each may be selected in order to provide a particular product. For example, all of the green tea ingredients may be obtained from natural sources and presented in a low to moderate dosage, in order to provide a natural product that can be used as a holistic treatment or nutritional supplement. Additionally, the green tea ingredients may be used in higher concentrations to impart a potency that is suitable for use in as a prescription medicine. Those of ordinary skill in the art will be able to determine a suitable therapeutically effective amount on an individual by individual basis.

One specific type of additional active ingredient that may be an aspect of the thermogenic component of the weight controlling composition is a metabolic stimulant. A wide range of compounds have been taught to produce a metabolism stimulating effect that may impart a weight reducing effect to a subject, and are known to those of ordinary skill in the art. Examples of specific metabolism stimulant compounds that may be used include without limitation, Ma Huang extract (ephedra), citrus aurantum extract (zhi shi, bitter orange, and synephrine), yohimbe extract (yohimbine), coleus extract (forskolin), and guarana (caffeine), as well as other stimulant compounds.

In accordance with the present invention, the components of the weight controlling composition can be present in variable amounts, where determining such amounts is easily within the ordinary skill of one in the art. The thermogenic component can have a daily dose range from about 500 mg to about 3,000 mg. In another aspect, the thermogenic component can have a daily dose of about 1,500 mg. Further, the green tea extract can have a daily dose range from about 350 mg to about 2,000 mg. More particularly, the green tea extract can have a daily dose of about 1,000 mg. Additionally, the calcium can have a daily dose range from about 150 mg to about 1,000 mg, which can be a daily dose of about 500 mg. In another aspect, the thermogenic component can be from about 30 wt % to about 70 wt % of the weight controlling composition. More particularly, the thermogenic component can be about 60 wt % of the weight controlling composition. In yet another aspect, the calcium can be present in a capsule at about 55 mg. In still another aspect, the green tea extract can be present in a capsule at about 110 mg.

The applicants have discovered that certain adverse health consequences result from prolonged stress as indicated by various physiological factors. As such, prolonged stress can lead to an increase in weight, which can lead to obesity. Accordingly, the present invention encompasses formulations and methods that can be used for moderating stress, or at least controlling the physiological indicators or symptoms thereof. Such formulations and methods can be used as an aspect of a multifaceted weight control system. In one aspect, the present invention can provide a stress modulating component with at least one cortisol modulator for controlling cortisol levels. Most often, controlling the cortisol level will result in reducing the cortisol level, but it also can include preventing the cortisol level from increasing.

Accordingly, various agents are known to provide a cortisol modulating or reducing effect when administered in a therapeutically effective amount. By way of example without limitation, such agents include, beta-sitosterol (phytosterol esters), epimedium, and phosphatidylserine. It has also been discovered that ashwagandha, garlic, magnolia bark, and L-theanine, as well as other forms of theanine, also have a cortisol modulating effect. Such compounds are known for a number of other beneficial properties, such as the immunostimulation properties of garlic, and the brainwave balancing properties of theanine. In one aspect of the invention, the cortisol modulator used in the weight controlling composition may be a member selected from the group consisting of: ashwagandha, beta-sitosterol, epimedium, garlic, magnolia bark, phosphatidylserine, theanine, and mixtures thereof, and extracts thereof. In one aspect, the epimedium can be from Epimedium koreanum, and can be a water extract of about 6:1. In a different aspect, the magnolia can be from Magnolia officinalis, and can be about a 4:1 extract. In another aspect, the cortisol modulator may be theanine. In yet another aspect, the cortisol modulator may be garlic. In a further aspect, the cortisol modulator may be magnolia bark. In yet a further aspect, the cortisol modulator may be ashwagandha. In an additional aspect, the cortisol modulator component of the weight loss composition may consist essentially of epimedium, magnolia bark, and/or theanine. In an additional aspect of the present invention, the weight controlling composition can contain a therapeutically effective amount of a cortisol modulator component which can include a magnolia bark extract, an epimedium extract, L-theanine, and beta-sitosterol.

The above-recited cortisol modulators may be individually included, or may be selectively combined in the formulation of the present invention in order to achieve a specific result. Moreover, the source and amount of each may be selected in order to provide a particular product. For example, all of the cortisol modulators may be obtained from natural sources and presented in a low to moderate dosage, in order to provide a natural product that can be used as a holistic treatment or nutritional supplement. Additionally, cortisol modulators from either natural or synthetic sources may be used in higher concentrations to impart a potency that is suitable for use in as a prescription medicine. Those of ordinary skill in the art will be able to determine a suitable therapeutically effective amount on an individual by individual basis.

Accordingly, in one aspect of the present invention, the cortisol modulator component of the formulation may be included in an amount of from about 2 wt % to about 100 wt % of the formulation. In another aspect, the amount may be from about 10 wt % to about 50 wt % of the formulation. In an aspect of the present invention, the weight controlling composition can include the cortisol modulator component in a daily dose range from about 300 mg to about 2000 mg. In another aspect, the cortisol modulator component can have a daily dosage of about 870 mg. In yet another aspect, the magnolia extract can have a daily dosage range from about 100 mg to about 600 mg. In accordance therewith, the magnolia extract can have a daily dosage of about 300 mg. In still another aspect, the epimedium extract can have a daily dosage range from about 100 mg to about 600 mg. In a more detailed aspect, the epimedium extract can have a daily dosage of about 300 mg. In a different aspect, the L-theanine can have a daily dosage range from about 50 mg to about 300 mg. In another more detailed aspect, the L-theanine can have a daily dosage of about 150 mg. In a further aspect, the beta-sitosterol can have a daily dosage range from about 40 mg to about 240 mg. Furthermore, the beta-sitosterol can have a daily dosage of about 120 mg.

Additionally, a number of other bioactive agents have been implicated in contributing to a general stress reducing effect, which may be beneficial in facilitating satiation while participating in a multifaceted weight control program. For example, many agents can impart an anti-anxiety (anxiolytic), or sedative effect. These anti-stress ingredients can include certain active agents, such as leucine, isoleucine, and valine, tyrosine, glutamine, 5-HTP, and precursors thereof, ginseng, suma (i.e. Brazilian ginseng), schisandra, rhodiola, astragalus, vitamin C, magnesium, B-complex vitamins, thiamin, riboflavin, pyridoxine, and pantothenic acid, kava, melatonin, valerian, and gotu kola, as well and many others. Such anti-stress agents can be included in the weight controlling composition of the present invention along with the thermogenic component, the cortisol modulator component, the carbohydrate craving controlling component, and the inert carrier. The specific type and amount of anti-stress ingredient, or mixture of anti-stress ingredients will depend on the specific properties desired for the final formulation. Those of ordinary skill in the art will be able to determine therapeutically effective amounts for specific ingredients based on the other ingredients in the formulation, and the mode of administration. Various combinations of such ingredients may be made, or individual ingredients may be selected and included in the present formulation, in order to achieve a specifically desired result. However, in one aspect, the amount of anti-stress ingredient used in the formulation may be from about 1 wt % to about 50 wt % of the formulation. In another aspect, the amount of anti-stress ingredient may be from about 5 wt % to about 30 wt % of the formulation. In yet another aspect, the amount of anti-stress ingredient may be less than about 1 wt % of the formulation.

The applicants have also discovered the additional benefit of curbing the carbohydrate cravings that an individual may experience while they are attempting to control their weight. After eating a carbohydrate-rich meal, the insulin level typically increases dramatically, and then drops again. Such a fluctuation in the insulin levels can induce a craving for carbohydrates soon after eating. Accordingly, the present invention encompasses formulations and methods that can be used for controlling carbohydrate cravings, or at least controlling the physiological indicators or symptoms thereof. Such formulations and methods can be used as an aspect of a multifaceted weight control system. In one aspect, the present invention can provide a carbohydrate craving controlling component. Most often, controlling the subject's carbohydrate craving will result in reducing the craving, but it also includes preventing the craving from increasing.

Various physiologically agents can control or aid in control of carbohydrate cravings. Such active agents can include, without limitation, a banaba leaf extract, vanadium, and chromium. In one aspect, banaba leaf extract can be from Lagerstroemia speciosa, and can further be a 10:1 leaf extract. Additionally, the banaba extract can be an oil based extract, and can include corosolic acid, where the corosolic acid can be about 1 wt %. Alternatively, extracts from the plant *Eriabotrya japonica* as recited in Applicant's copending U.S. patent application Ser. No. 10/420,347, file on Apr. 21, 2003, which is incorporated herein by reference, as well as extracts from the plant *fructus chaenomelis* may be used. Also, the vanadium can be in the form of pharmaceutically acceptable salt of vanadium, such as a vanadyl or vanadate, which can include vanadyl sulfate, sodium vanadate, and others. Further, the chromium can be in the form of a pharmaceutically acceptable salt of chromium, such as chromium polynicotinate, chromium picolinate, chromium chloride, and the like. Also, chromium can be in the form of a chelate, such as a chromium III amino acid chelate. In one aspect, the weight controlling composition can contain a therapeutically effective amount of a carbohydrate craving controller component which includes a banaba leaf extract, vanadium and chromium.

In addition to the above-recited carbohydrate craving controlling ingredients, the present invention may include a therapeutically effective amount of 5 HTP, or other amino acids which mimic is behavior in vivo, or that work to stimulate serotonin production. 5 HTP is a serotonin precursor. Serotonin acts on the reward center of the brain an has the effect of reducing the cravings for pleasure induced by the consumption of carbohydrates. Thus, in one aspect of the present invention, the carbohydrate craving controller may include both a blood glucose controlling or normalizing ingredient, as well as a serotonin stimulating or producing ingredient.

In accordance with the present invention, the amount and dosage of the carbohydrate craving controller component and the contents thereof can vary as long as the composition or dosing regimen can curb the cravings of a subject. In one aspect of the present invention, the carbohydrate craving controller component can have a daily dosage range from about 10 mg to about 65 mg. In another aspect, the carbohydrate craving controller component can have a daily dosage range from about 32 mg. In yet another aspect, the banaba leaf extract can have a daily dosage range from about 10 mg to about 64 mg. In a further aspect, the banaba leaf extract can have a daily dosage of about 32 mg. In still another aspect, the chromium can have a daily dosage range from about 66.7 mcg to about 400 mcg. In a more detailed aspect, the chromium can have a daily dosage of about 200 mcg. In a different aspect, the vanadium can have a daily dosage range from about 10 mcg to about 60 mcg. In a further aspect, the vanadium can have a daily dosage of about 30 mcg.

Additionally, it has also been discovered that extracts of Sea Buckthorn can provide activity in controlling the body weight of a subject when administered in a therapeutically effective amount. Further, Sea Buckthorn extracts can provide activity in controlling and/or lowering the serum lipid concentrations of a subject, which may contribute to the body weight controlling function. Without wishing to be bound by theory, it is thought that the weight reducing activity can be attributed, at least in part, to the effect that a Sea Buckthorn extract has on stimulating production and/or release of cholecystokinin (CCK) in the subject, which can increase the serum concentration of cholecystokinin. As discussed in U.S. Pat. Nos. 6,207,638, and 6,429,190, each of which is incorporated herein by reference, cholecystokinin is a peptide that is released following the consumption of food, and is known to induce feelings of satiety and fullness. Cholecystokinin may also be involved in the rate of gastric emptying. Therefore, cholecystokinin stimulation may produce an appetite suppressing effect. Accordingly, in an aspect of the present invention, the weight controlling composition can include a Sea Buckthorn extract. In another aspect, the Sea Buckthorn extract may be present in a therapeutically effective amount.

In another aspect of the present invention, the thermogenic component, the cortisol modulator component, and the carbohydrate craving controller component may be combined with inert carriers and other inactive ingredients in order to create a specific dosage form. Accordingly, the inert carrier may be selected from calcium carbonate, calcium silicate, calcium magnesium silicate, calcium phosphate, kaolin, sodium hydrogen carbonate, sodium sulfate, barium carbonate, barium sulfate, magnesium sulfate, magnesium carbonate, activated carbon, water, isopropyl alcohol, ethyl alcohol, polyvinyl pyrrolidone, propylene glycol, polyethylene glycol stearyl alcohol, stearic acid, sorbitan monooleate, microcrystalline cellulose, sodium carboxymethyl cellulose, hydroxyethyl cellulose, hydroxypropyl cellulose, hydroxypropyl methylcellulose, sorbitol, mannitol, xylitol, starches, gelatins, lactose, acacia, carbomer, dextrin, guar gum, lactose, liquid glucose, maltodextrin, polymethacrylates, and combinations thereof, as well as other carrier well known in the art. In one aspect, the weight controlling composition can contain an effective amount of an inert carrier, where the inert carrier can be selected from gelatin, microcrystalline cellulose, magnesium stearate, silicon dioxide, and combinations thereof.

The amount of the pharmaceutically acceptable carrier used in the weight controlling composition may vary depending on the characteristics of the final product desired. Accordingly, the number and amount of other desired ingredients, as well as the size of the final product will impact the amount of carrier included in the composition. However, the amount of pharmaceutically acceptable carrier will generally be from about 1 wt % to about 10 wt % of the composition. Additionally, depending on the dosage form to be administered, the carrier can be present up to about 90 wt % of the composition.

Other traditional ingredients which do not interfere with the function of the bioactive agent may optionally be included as part of the carrier, such as lubricants, binders, buffers, preservatives, tonicity adjusting agents, and polymers for adjusting viscosity or for use as extenders, and excipients, and the like. Other conventional additives include humectants, emollients, lubricants, stabilizers, dyes, providing the additives do not interfere with the therapeutic properties of the cortisol modulating composition. Numerous examples of specific agents for each type of ingredient will be well recognized by one of ordinary skill in the art, and may be employed in view of a specific result or formulation that is to be achieved.

In formulating a weight controlling composition, it is important to note that there are not rigid requirements for the proportionalities of the various components with each other. As known to one of ordinary skill in the art, the ratios of the components can vary and still provide the intended effect. Additionally, the ratio of components that is effective for one subject may not be effective for another, which can allow for various ratios of the ingredients to impart weight control to different subject. As such, the thermogenesis component and the cortisol modulator component can be present in a weight ratio of from about 3:2 to about 5:3. Additionally, the thermogenic component and the carbohydrate craving controller can be present in a weight ratio of from about 50:1 to about 300:6.4. Furthermore, the cortisol modulator component and the carbohydrate craving controller can be present in a weight ratio of from about 30:1 to about 200:6.4.

In another aspect, the composition may also include other active agents in addition to the thermogenic component, the cortisol modulator component, and the carbohydrate craving controller component, which are included to provide an intended effect, or a specifically desired result. Both natural and synthetically produced active agents may be included. Those of ordinary skill in the art will be able to select from a wide range of specific ingredients in order to provide a desired therapeutic effect. In one aspect, the additional active ingredient may be a natural ingredient, such as an herbal or botanical extract. In another aspect, the additional active ingredient may be synthetically produced. In still another aspect of the invention, the composition may further include an active ingredient selected from the group consisting of herbal extracts, botanical extracts, vitamins, minerals, amino acids, proteins, enzymes, and combinations thereof.

Examples of herbal extract agents and botanical extract agents that may be added to the weight controlling composition include without limitation, Ginseng, *Ginko Biloba*, Dong Quai, Hawthorn berry, St. John's Wort, Saw Palmetto, Kava Kava, Rose Hips, *Echinacea*, Licorice Root, Grape seed, Chammomile, *Aloe Vera*, Cinnamon Bark, Cordyceps, Ho Shou Wu, Dandelion, *Gynostemma*, mushrooms, Dan Shen, etc. Additional examples of herbal extract can include, without limitation, Causena Lansium, *Crocus Sativus*, Danshen (*saliva miltiorrhize*), Dongui (Radix angelicae sinesis), *Eucommia*, Evening primrose, *Gastrodia elata*, Hopes, Lemon balm, Mishmi bitter (*coptis sinesis*), Morning star (*Uncaria rhychophylla*), Passion flower, Physostigmine, *Securinega Suffructicosa, Scutellaria baicalensis*, Siberian cork tree (*phellodendron amurense*), Skullcap, Valerian, and mixtures thereof.

In an aspect of the present invention, fruit extracts and vegetable extracts can be included in the weight controlling composition. Examples of fruit extracts may include apple, apricot, banana, blue berry, cranberry, cherry, fig, grape, grapefruits, hawthorn berry, huckleberry, kiwi fruit, kumquat, lemon, lime, mango, melon, nectarine, noni fruit, orange, papaya, peach, pear, persimmon, pineapple, plum, pomegranate, raspberry, strawberry, tangerine, watermelon, and mixtures thereof. Additionally, examples of the vegetable extracts may include artichoke, avocado, asparagus, beans, bell pepper, broccoli, brussels sprout, cabbage, cauliflower, carrot, celery, cucumber, eggplant, green bean, lettuce, onion, parsley, pea, potato, pumpkin, radish, radicchio, rhubarb, spinach, tomato, zucchini, and mixtures thereof.

Some examples of acceptable vitamins that can be added to the weight controlling composition can include both water-soluble and oil soluble vitamins. Water-soluble vitamins can include B1, B2, B3, B4, B5, B6, B12, B13, B15, B17, biotin, choline, folic acid, inositol, para-amino benzoic acid (PABA), Vitamin C, Vitamin P, and mixtures thereof. Additionally, oil soluble vitamins include Vitamin A, Vitamin D, Vitamin E, Vitamin K, and mixtures thereof.

Also, examples of acceptable minerals that can be present in the weight controlling composition can include, potassium, iron, phosphorous, magnesium, zinc, copper and mixtures thereof, as well as any other minerals essential to the human body. Accordingly, many of these minerals may be present as pharmaceutically acceptable salts or chelates.

Additionally, examples of acceptable amino acids that can be formulated with the weight controlling composition include but are not limited to alanine arginine, carnitine, gamma-aminobutyric acid (GABA), glutamine, glycine, histidine, 5-HTP, precursors thereof, lysine, methionine, N-acetyl systeine, ornithine, phenylalanine, taurine, tyrosine, valine, and mixtures thereof.

Additionally, the weight controlling composition can include additional antioxidants. Specific examples of acceptable antioxidants which can be incorporated into the composition may include but are not limited to beta-carotene, coenzyme Q10, grapnel, and mixtures thereof.

In addition to the aforementioned compositions, the green tea, the epimedium, the banaba, and/or the magnolia, or any other plants utilized in the present invention may be derived from any part of these plants, and may take a variety of physical forms, especially as extracts. In one aspect, the extracts can come from the fruits, leaves, flowers, stems, bark, and or they other aspect of the plants. However, in one aspect the extract may be an oil. In another aspect, the extract may be a solid, or powder. In yet another aspect, the extract may be a water-soluble infusion extract. In a further aspect, the extract may be a dry, or lyophilized powder. In an additional aspect, the extract may be an emulsion.

Additionally, other ingredients for preparing different types of dosage forms may be added to the mixture before it is ultimately conveyed into the final dosage form. For example, when produced as an oral dosage, such as a chewable table, lozenge, or liquid, flavoring agents, and sweetening agents may be added. Flavoring agents may be chosen based upon the desired flavor. Sweetening agents may also be any type of general sweetening agent such as sugar, stevia, sucralose, saccharin, aspartame, and/or other natural sweeteners. The dosage can then be placed in final form by any additional processing measures required by the specific form, such pressing for tablets, capsules, etc.

The weight controlling composition may be provided as an oral dosage form. A variety of oral dosage forms are well known to those of ordinary skill in the art, and specific formulation ingredients may be selected in order to provide a specific result. Examples of oral dosage forms include without limitation, oral dosage forms such as tablets, capsules, gel capsules, liquids, syrups, elixirs, and suspensions. Additionally, oral dosage forms encompass food preparations, such as bars and beverages. In another aspect of the present invention, the weight controlling composition can be an oral composition. Accordingly, the oral composition can be in a form selected from a tablet, a capsule, a gel capsule, a liquid, syrup, a elixir, and a suspension. More particularly, the oral composition can be a capsule. In accordance therewith, the capsule can include the ingredients in the amounts as follows: about 50 mg of calcium, about 20 mcg chromium, about 110 mg green tea extract, about 30 mg magnolia extract, about 30 mg epimedium, about 15 mg L-theanine, about 10 mg beta-sitosterol, about 5 mg banaba leaf extract, and about 5 mcg vanadium. Additionally, the capsule can contain an inert carrier, where the amount of the inert carrier can be varied depending on desired final characteristics of the capsule, such as size, dissolution parameters, etc.

The weight controlling composition may also be provided as a transdermal or parenteral dosage form. A number of specific transdermal and parenteral dosage forms are well known to those of ordinary skill in the art. Examples of transdermal dosage forms include without limitation lotions, gels, creams, pastes, ointments, transmucosal tablets, adhesive devices, adhesive matrix-type transdermal patches, liquid reservoir transdermal patches, etc. Also, parenteral dosage forms may be formulated to provide efficient delivery of a weight controlling composition to a subject.

An additional embodiment of the present invention provides methods for controlling the weight of a subject in need thereof. Such methods can include the steps of: elevating thermogenic activity within the subject; controlling the subject's carbohydrate cravings; and controlling the subject's cortisol level. In one aspect, all of these steps can occur simultaneously. In yet another aspect, all of the steps can be induced by administering a weight controlling composition as recited herein. In yet another aspect, the method can further include the step of increasing the subject's level of exercise. In still another aspect, the method can further include the step of providing the subject with a healthy diet. In the methods described herein, controlling the weight can either be reducing the weight of the subject, or is preventing the weight of the subject from increasing. In a further aspect, controlling the subject's carbohydrate cravings can be reducing the subject's carbohydrate cravings. Furthermore, controlling the subject's cortisol level can be reducing the subject's cortisol level.

In another aspect of the present invention, the steps of the above recited method are not required to be facilitated in concert. Accordingly, these steps can occur in any sequence according to a pre-designed weight control system. As such, the individual components of the weight control composition can be administered separately in a multifaceted weight controlling system. Thus, in one aspect of the present invention, the carbohydrate craving controlling component can be administered separately. In another aspect, the thermogenic component can be administered separately. In yet another aspect, the cortisol modulator component can be administered separately. Additionally, any of these components can be administered simultaneously in a variable control release formulation. As such, a composition can include the thermogenic component and the cortisol modulator component, where each of these components is configured to be released separately in series. Alternatively, any of the components can be contained within a variable control release formulation configured for sequential release therefrom.

In accordance with the compositions and methods described herein, the weight controlling composition, or any of the individual components thereof can be administered on a daily basis as needed or according to a specific and customized dosing regimen. Additionally, in any of the dosing regimen schemes that follow, reference to the weight controlling composition can include any of the individual components thereof, such as the thermogenic component, the cortisol modulator component, and/or the carbohydrate craving controlling components. In one aspect, the weight loss composition, can be administered at least once a day. In another aspect, the weight loss composition, can be administered multiple times a day. In a further aspect, administration may occur at least 3 times a day. In yet another aspect, the weight loss composition, can be administered either a specified amount of time prior to, at about the same time the subject consumes a meal.

Of course, the duration of the weight loss regimen can be customized to address the particular needs of the subject engaged in the program. For example, in some aspects, the composition can be administered in a regimen having a duration of at least one week. In another aspect, the weight loss composition can be administered in a regimen having a duration of at least one month. Furthermore, the weight loss composition can be administered in a regimen having a duration of from about 3-24 months. Additionally, administering the composition to the subject can be part of a sustained dosing regimen which lasts indefinitely following the attainment of the desired weight loss for maintenance purposes.

EXAMPLES

The following Examples are illustrative of specific embodiments of active ingredient combinations that may be presented in a weight controlling composition in accordance with the present invention. Notably, the recited active ingredients may be combined with other inactive ingredients, such as binders, carriers, etc. to provide a specific final dosage form. Further, various parameters of the final dosage form, including the size, specific ingredients, and concentration of each, may be adjusted to provide a particular dose of specific bioactive agents. However, no limitation on the present invention is to be inferred thereby.

Example 1

A Cortisol Controlling Component Formulation

| Formulation | Amount in % w/w |
|---|---|
| Magnolia bark extract (*Magnolia Officinalis*) | 38% |
| Epimedium (*Epimedium koreanum*) | 29% |
| L-Theanine (Green tea extract) | 19% |
| Beta-Sitosterol | 12% |
| Phosphatidylserine | 2% |

Example 2

A Cortisol Controlling Component Formulation

| Formulation | Amount in % w/w |
| --- | --- |
| Ashwagandha (*Withania somnifera*) | 38% |
| Garlic | 29% |
| L-Theanine (Green tea extract) | 19% |
| Beta-Sitosterol | 12% |
| Phosphatidylserine | 2% |

Example 3

A Cortisol Controlling Component Formulation

| Formulation | Amount in % w/w |
| --- | --- |
| Magnolia bark extract (*Magnolia Officinalis*) | 90% |
| Phosphatidylserine | 10% |

Example 4

A Cortisol Controlling Component Formulation

| Formulation | Amount in % w/w |
| --- | --- |
| Magnolia bark extract (*Magnolia Officinalis*) | 75% |
| L-Theanine (Green tea extract) | 25% |

Example 5

A Thermogenic Component Formulation

| Formulation | Amount in % w/w |
| --- | --- |
| Ephedra (*Ephedra sinensis, Ma Huang*) | 5% |
| Green tea extract | 75% |
| Calcium (dicalcium malate) | 20% |

Example 6

A Thermogenic Component Formulation

| Formulation | Amount in % w/w |
| --- | --- |
| Green tea extract | 60% |
| Calcium (dicalcium malate) | 30% |
| Guarana (*Paullinia cupana*) | 10% |

Example 7

A Thermogenic Component Formulation

| Formulation | Amount in % w/w |
| --- | --- |
| Green tea extract | 50% |
| Calcium (dicalcium malate) | 50% |

Example 8

A Carbohydrate Craving Controlling Component Formulation

| Formulation | Amount in % w/w |
| --- | --- |
| Banaba extract (*Lagerstroemia speciosa*) | 99.5% |
| Chromium (chromium chelate) | 0.250% |
| Vanadium (vanadyl sulfate) | 0.250% |

Example 9

A Carbohydrate Craving Controlling Component Formulation

| Formulation | Amount in % w/w |
| --- | --- |
| Banaba extract (*Lagerstroemia speciosa*) | 99.8% |
| Chromium (chromium chelate) | 0.1% |
| Vanadium (vanadyl sulfate) | 0.1% |

Example 10

A Weight Controlling Composition

| Formulation | Amount in % w/w |
| --- | --- |
| Green tea extract | 50% |
| Calcium (dicalcium malate) | 15% |
| Chromium (chromium chelate) | 0.01% |
| Vanadium (vanadyl sulfate) | 0.005% |
| Magnolia bark extract (*Magnolia officinalis*) | 15% |
| Epimedium (*Epimedium koreanum*) | 14% |
| L-theanine | 7% |
| Beta-sitosterol | 6% |
| Banaba extract (*Lagerstroemia speciosa*) | 1.5% |
| Carrier (gelatin, microcrystalline cellulose, magnesium stearate) | balance |

Example 11

A Weight Controlling Composition

| Formulation | Amount per serving |
| --- | --- |
| Green tea extract | 333.3 mg |
| Calcium (dicalcium malate) | 166.7 mg |
| Chromium (chromium chelate) | 66.7 mcg |
| Vanadium (vanadyl sulfate) | 10 mcg |

-continued

| Formulation | Amount per serving |
|---|---|
| Magnolia bark extract (*Magnolia officinalis*) | 100 mg |
| Epimedium (*Epimedium koreanum*) | 100 mg |
| L-theanine | 50 mg |
| Beta-sitosterol | 40 mg |
| Banaba extract (*Lagerstroemia speciosa*) | 10.7 mg |
| Carrier (gelatin, microcrystalline cellulose, magnesium stearate) | 50 mg |

Example 12

A Weight Controlling Composition

| Formulation | Amount per capsule |
|---|---|
| Calcium (dicalcium malate) | 55.6 mg |
| Chromium (chromium chelate) | 22.3 mcg |
| Green tea extract | 111 mg |
| Magnolia bark extract (*Magnolia officinalis*) | 33.3 mg |
| Epimedium extract (*Epimedium koreanum*) | 33.3 mg |
| L-theanine | 16.36 mg |
| Beta-sitosterol | 13.3 mg |
| Banaba extract (*Lagerstroemia speciosa*) | 3.57 mg |
| Vanadium (vanadyl sulfate) | 3.3 mcg |
| Carrier (gelatin, microcrystalline cellulose, magnesium stearate) | 20 mg |

Example 13

A Weight Controlling Composition

| Formulation | Daily dose |
|---|---|
| Calcium (dicalcium malate) | 55.6 mg |
| Chromium (chromium chelate) | 200 mcg |
| Green tea extract | 1,000 mg |
| Magnolia bark extract (*Magnolia officinalis*) | 300 mg |
| Epimedium extract (*Epimedium koreanum*) | 300 mg |
| L-theanine | 150 mg |
| Beta-sitosterol | 120 mg |
| Banaba extract (*Lagerstroemia speciosa*) | 32 mg |
| Vanadium (vanadyl sulfate) | 30 mcg |
| Carrier (gelatin, microcrystalline cellulose, magnesium stearate) | NA |

Example 14

A Method of Controlling the Weight of a Subject

A human subject being of average weight is treated by the following procedure. In this example, the weight controlling serving of Example 11 is provided. The dosing regimen includes administering the serving orally 3 times per day, where the serving is taken at about the same time as meals are consumed. After administration of the dosing regimen with the weight controlling composition, the subject's weight can be controlled and is prevented from increasing.

Example 15

A Method of Reducing the Weight of a Subject

A human subject being overweight is treated by the following procedure. In this example, the capsule formulation of Example 12 is provided. In this regimen, 3 capsules are administered orally to a human subject at breakfast, lunch, and dinner. After treatment with the weight controlling composition, the subject's weight can be reduced.

Example 16

A Method of Reducing the Weight of an Obese Subject

A human subject being obese is treated by the following procedure. In this example, the daily dosage of Example 13 is provided. The daily dosage is administered orally to the obese subject accordingly to a predetermined regimen. After treatment with the weight controlling composition, the obese subject's weight can be reduced.

It is to be understood that the above-described examples are only illustrative of the application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and/or preferred embodiments of the invention, it will be apparent to those of ordinary skill in the art that these examples not intended to be limiting in nature.

What is claimed is:

1. A weight controlling composition for administration to a subject in need thereof comprising:
    a therapeutically effective amount of a thermogenic component which includes calcium and a green tea extract (*Camellia senesis*);
    a therapeutically effective amount of a cortisol modulator component which includes a *Magnolia* bark extract, an *Epimedium* extract, L-theanine, and beta-sitosterol;
    a therapeutically effective amount of a carbohydrate craving controlling component which includes a banaba leaf extract (Lagerstroemia speciosa), MuGua extract (*Fructus Chaenomelis*), Pi pa ye extract (*Eriobotrya japonica*), vanadium, and chromium, and an inert carrier.

2. A composition as in claim 1, wherein the thermogenic component has a daily dosage range from about 500 mg to about 3,000 mg.

3. A composition as in claim 2, wherein the daily dosage is about 1,500 mg.

4. A composition as in claim 1, wherein the cortisol modulator component has a daily dosage range from about 300 mg to about 2000 mg.

5. A composition as in claim 4, wherein the daily dosage is about 870 mg.

6. A composition as in claim 1, wherein the carbohydrate craving controller component has a daily dosage range of about 10 mg to about 65 mg.

7. A composition as in claim 6, wherein the daily dosage is about 32 mg.

8. A composition as in claim 1, wherein the inert carrier is selected from the group consisting of gelatin, microcrystalline cellulose, magnesium stearate, silicon dioxide, and combinations thereof.

9. A composition as in claim 1, wherein the thermogenic component and the cortisol modulator component are present in a weight ratio of from about 3:2 to about 5:3.

10. A composition as in claim 1, wherein the thermogenic component and the carbohydrate craving controller component are present in a weight ratio of from about 50:1 to about 300:6.4.

11. A composition as in claim 1, wherein the cortisol modulator component and the carbohydrate craving controller are present in a weight ratio of from about 30:1 to about 200:6.4.

12. A composition as in claim 1, wherein the weight controlling composition is in oral dosage form.

13. A composition as in claim 12, wherein the oral dosage form is selected from the group consisting of granules, powders, tablets, capsules, gel capsules, liquids, syrups, elixirs, suspensions, and combinations thereof.

14. A composition as in claim 12, wherein the oral dosage form is a capsule.

15. A method of controlling the weight of a subject comprising administering in an effective amount a composition as in claim 1 to the subject.

16. The method of claim 15, wherein the composition is administered as part of a regimen having a duration of at least one week.

17. The method of claim 15, wherein the composition is administered as part of a regimen having a duration of at least one month.

18. The method of claim 15, wherein the composition is administered as part of a regimen having a duration of about three months to about twenty-four months.

19. A method as recited in claim 15, further comprising increasing the subject's level of weekly exercise.

20. A method as recited in claim 15, further comprising restricting either a type or amount of food ingested by the subject on a daily basis.

* * * * *